United States Patent
Fujisawa et al.

(10) Patent No.: US 6,818,719 B2
(45) Date of Patent: Nov. 16, 2004

(54) POLYMERS AND OPHTHALMIC LENSES IN WHICH THEY ARE USED

(75) Inventors: Kazuhiko Fujisawa, Otsu (JP); Naoki Shimoyama, Otsu (JP); Mitsuru Yokota, Otsu (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 10/398,919

(22) PCT Filed: Sep. 25, 2001

(86) PCT No.: PCT/JP01/08282

§ 371 (c)(1),
(2), (4) Date: Apr. 11, 2003

(87) PCT Pub. No.: WO02/31007

PCT Pub. Date: Apr. 18, 2002

(65) Prior Publication Data

US 2004/0014921 A1 Jan. 22, 2004

(30) Foreign Application Priority Data

Dec. 10, 2000 (JP) ........................................ 2000-311885

(51) Int. Cl.[7] .............................................. C08F 120/10
(52) U.S. Cl. ................. 526/323.2; 526/279; 526/307.5; 526/307.7
(58) Field of Search ............................ 526/279, 307.5, 526/307.7, 320, 323.2

(56) References Cited

U.S. PATENT DOCUMENTS 4,139,513 A    2/1979  Tanaka et al.
4,139,548 A    2/1979  Tanaka et al.
4,139,692 A    2/1979  Tanaka et al.
4,433,125 A    2/1984  Ichinohe et al.

FOREIGN PATENT DOCUMENTS

JP    50-87184        7/1975
JP    11-326847       11/1999
JP    2000-191730     7/2000

*Primary Examiner*—Helen L. Pezzuto

(57) ABSTRACT

Polymers of high oxygen permeability and a low modulus of elasticity and ophthalmic lenses and contact lenses using the same are provided. The polymers are characterized in that they are obtained by copolymerizing 5 to 90 parts by weight of a monomer (SiMAA) represented by the formula below, 5 to 90 parts by weight of 3-tris (trimethylsiloxy) silyl propyl methacrylate (TRIS), 5 to 70 parts by weight of N,N-dimethyl acrylamide (DMAA) and 0.1 to 3 parts by weight of monomer having two or more copolymerizable carbon-carbon unsaturated bonds in 1 molecule (provided that the total quantity of SiMAA, TRIS and DMAA is 100 parts by weight and that the total quantity of SiMAA and TRIS is 30 to 95 parts by weight), and which are used for ophthalmic lenses.

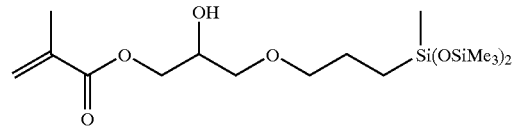

5 Claims, No Drawings

POLYMERS AND OPHTHALMIC LENSES IN WHICH THEY ARE USED

TECHNICAL FIELD

This invention relates polymers and said polymers are particularly suited to use in ophthalmic lenses such as contact lenses, intraocular lenses and artificial corneas.

PRIOR ART

Conventionally, polymers obtained by copolymerizing monomers having silicon groups and hydrophilic monomers have been used as polymers for ophthalmic lenses.

For example, polymers are known that are obtained by copolymerizing 3-tris (trimethylsiloxy) silyl propyl methacrylate with N,N-dimethyl acrylamide. Although these polymers have the merit of high oxygen permeability, they have a high modulus of elasticity, for which reason there is the drawback, for example, that they feel uncomfortable when they are used for contact lenses.

Further, polymers are known that are obtained by copolymerizing siloxanyl monomers represented by the formula below with N,N-dimethyl acrylamide. Although these polymers have a low modulus of elasticity, they have the drawback of poor oxygen permeability.

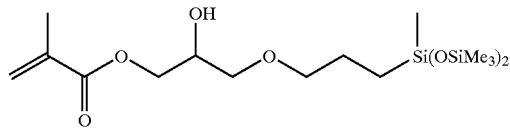

DISCLOSURE OF THE INVENTION

This invention has the objective of providing polymers of high oxygen permeability and a low modulus of elasticity and ophthalmic lenses and contact lenses in which they are used.

In order to achieve this objective, this invention has the structure described below.

They are polymers characterized in that they are obtained by copolymerizing 5 to 90 parts by weight of a monomer represented by the formula below (hereafter referred to as SiMAA), 5 to 90 parts by weight of 3-tris (trimethylsiloxy) silyl propyl methacrylate (hereafter referred to as TRIS), 5 to 70 parts by weight of N,N-dimethyl acrylamide (hereafter referred to as DMAA) and 0.1 to 3 parts by weight of monomer having two or more copolymerizable carbon-carbon unsaturated bonds in 1 molecule (provided that the total quantity of SiMAA, TRIS and DMAA is 100 parts by weight and that the total quantity of SiMAA and TRIS is 30 to 95 parts by weight).

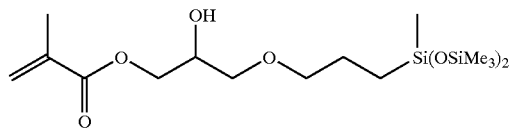

EMBODIMENT OF THE INVENTION

We shall now describe the embodiment of this invention.

The polymers of this invention contain a total of 100 parts by weight of SiMAA, TRIS and DMAA, including the two siloxanyl monomers, SiMAA in an amount of 5 to 90 parts by weight and TRIS in an amount of 5 to 90 parts by weight, as the copolymerization components. The total content of these siloxanyl monomers is 30 to 95 parts by weight.

Further, the polymers of this invention contain a total of 100 parts by weight of SiMAA, TRIS and DMAA, and 5 to 70 parts by weight of DMAA as the copolymerization components. Preferably, the total content of SiMAA and TRIS is 40 to 80 parts by weight and the content of DMAA is 20 to 60 parts by weight. Most preferably, the SiMAA is 5 to 59 parts by weight, TRIS is 5 to 59 parts by weight (provided that the total content of SiMAA and TRIS is 50 to 64 parts by weight) and DMAA is 36 to 50 parts by weight.

By setting the content of each monomer in the ranges described above, polymers are obtained that are endowed with both high oxygen permeability and a low modulus of elasticity (i.e., pliability) and that have excellent mechanical properties and excellent resistance to disinfecting solutions and cleaning solutions.

Further, by using 0.1 to 3 parts by weight of monomer having two or more copolymerizable carbon-carbon unsaturated bonds in 1 molecule per a total content of 100 parts by weight of SiMAA, TRIS and DMAA as the copolymerization components in the polymers of this invention, excellent mechanical properties are obtained and excellent resistance to disinfecting solutions and cleaning solutions are obtained. The copolymerization ratio of monomer having two or more copolymerizable carbon-carbon unsaturated bonds in 1 molecule should be greater than 0.3 part by weight, and, preferably, greater than 0.5 part by weight.

The polymer of this invention may also contain ultraviolet absorbents, pigments and colorants. Further, ultraviolet absorbents, pigments and colorants having polymerizable groups are copolymerized and may be contained in the polymer.

In order to facilitate polymerization in (co)polymerization of the monomers of this invention, the addition of thermal polymerization initiators and photopolymerization initiators of which peroxides and azo compounds are representative is desirable. When thermal polymerization is performed, a substance having optimum decomposition characteristics at the desired reaction temperature is selected and used. In general, azo initiators and peroxide initiators having 10 hour half-life temperatures of 40 to 120° C. are suitable. Carbonyl compounds, peroxides, azo compounds, sulfur compounds, halogen compounds and metal salts can be cited as photopolymerization initiators. These polymerization initiators can be used individually or in mixtures and are used in quantities up to approximately 1 part by weight.

A polymerization solvent can be used in (co)polymerization of the polymers of this invention. Various organic and inorganic solvents can be used as the solvents and there are no particular limitations on them. Examples that can be cited include water, various alcohol solvents such as methanol, ethanol, propanol, 2-propanol, butanol and tert-butanol, various aromatic hydrocarbon solvents such as benzene, toluene and xylene, various aliphatic hydrocarbon solvents such as hexane, heptane, octane, decane, petroleum ether, kerosene, ligroin and paraffin, various ketone solvents such as acetone, methyl ethyl ketone and methyl isobutyl ketone, various ester solvents such as ethyl acetate, butyl acetate, methyl benzoate and dioctyl phthalate and various glycol ether solvents such as diethyl ether, tetrahydrofuran, dioxane, ethylene glycol dialkyl ethers, diethylene glycol alkyl ethers, triethylene glycol dialkyl ethers, tetraethylene glycol dialkyl ethers and polyethylene glycol dialkyl ethers. They can be used individually or in mixtures.

Usual methods can be used as the polymerization methods and molding methods of the polymers of this invention. For example, there is a method in which they are molded into rods or plates and are then processed to the desired shapes by cutting processing, there is the mold polymerization method and there is the spin cast method.

As an example, we shall now describe the case in which the polymer of this invention is obtained by the mold polymerization method.

The monomer composition is filled into the space of two molds having a fixed shape. Photopolymerization or thermal polymerization is performed and it is formed to the shape of the mold. The mold can be made of resin, glass, ceramics or metal. In the case of photopolymerization, a material that is optically transparent is used, and, ordinarily, resin or glass is used. In many cases, when a polymer is manufactured, a space is formed by the two opposing molds and the space is filled with the monomer composition. Depending on the shape of the mold and the properties of the monomer composition, a gasket may be used for the purpose of conferring a fixed thickness on the polymer and of preventing leakage of the filled monomer composition solution. The mold into the space of which the monomer composition is filled is then irradiated with active light rays such as ultraviolet rays or is introduced into an oven or a solution tank and is heated to polymerize the monomers. The two methods can also be used in combination, with thermal polymerization being performed after photopolymerization, or, conversely, it can be photopolymerization being performed after thermal polymerization. In the case of photopolymerization, for example, light containing a large quantity of ultraviolet rays is usually irradiated for a short time (ordinarily 1 hour or less) using a mercury lamp or an insect attraction lamp as the light source. When thermal polymerization is performed, the temperature is gradually raised from close to room temperature, being increased to a temperature of 60° C. to 200° C. over a period of several hours to several tens of hours. These conditions are desirable for the purpose of maintaining the optical homogeneity and quality of the polymer and for increasing reproducibility.

The molded product in which the polymer of this invention is used can be subjected to modification treatments by various methods. It is desirable to perform said modification treatment for the purpose of increasing aqueous wetting property of the surface.

Specific modification methods can include the use of electromagnetic waves (including light) irradiation, plasma irradiation, chemical vapor deposition treatments such as vaporization and sputtering, thermal treatments, treatment with bases, treatment with acids and other suitable surface treatment agents, and combinations of these treatments. Of these modification procedures, treatment with bases and treatment with acids are desirable because they are simple.

Examples of treatments with bases and treatments with acids that can be cited include a method in which the molded product is brought into contact with a basic or acidic solution and a method in which the molded product is brought into contact with a basic or acidic gas. More specific examples include, for example, methods in which the molded product is immersed in a basic or acidic solution, methods in which a basic or acidic solution or a basic or acidic gas is sprayed at the molded product, methods in which a basic or acidic solution is applied to the molded product with a spatula or brush and methods in which a basic or acidic solution is applied to the molded product by the spin coating method or the dip coating method. The method whereby great modifying effects can be obtained the most simply is the method in which the molded product is immersed in a basic or acidic solution.

There are no particular limitations on temperature when the molded product is immersed in the basic or acidic solution. However, the procedure is usually performed in a temperature range of on the order of −50° C. to 300° C. When workability is considered, a temperature range of −10° C. to 150° C. is preferable and −5° C. to 60° C. is more preferable.

The optimum period for immersion of the molded product in the basic or acidic solution varies depending on the temperature. In general, a period of up to 100 hours is desirable, a period of up to 24 hours is more preferable and a period of up to 12 hours is most preferable. When contact time is too long, workability and productivity deteriorate and there are instances in which there are such deleterious effects as decrease of oxygen permeability and decrease of mechanical properties.

The bases that can be used include alkali metal hydroxides, alkaline earth metal hydroxides, various carbonates, various borates, various phosphates, ammonia, various ammonium salts, various amines and high molecular weight bases such as polyethylene imines and polyvinyl amines. Of these, alkali metal hydroxides are the most desirable because of their low cost and their great treatment effectiveness.

The acids that can be used include various inorganic acids such as sulfuric acid, phosphoric acid, hydrochloric acid and nitric acid, various organic acids such as acetic acid, formic acid, benzoic acid and phenol and high molecular weight acids such as polyacrylic acids and polystyrene sulfonic acids. Of these, high molecular weight acids are the most desirable because of their great treatment effectiveness and because they have little deleterious effect on other physical properties.

Various inorganic and organic solvents can be used as solvents of the basic and acidic solutions. For example, they can include water, various alcohols such as methanol, ethanol, propanol, 2-propanol, butanol, ethylene glycol, diethylene glycol, triethylene glycol, tetraethylene glycol, polyethylene glycol and glycerol, various aromatic hydrocarbons such as benzene, toluene and xylene, various aliphatic hydrocarbons such as hexane, heptane, octane, decane, petroleum ether, kerosene, ligroin and paraffin, various ketones such as acetone, methyl ethyl ketone and methyl isobutyl ketone, various esters such as ethyl acetate, butyl acetate, methyl benzoate and dioctyl phthalate, various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether, various nonprotonic polar solvents such as dimethylformamide, dimethylacetamide, N-methyl-2-pyrrolidone, dimethylimidazolidinone, hexamethyl phosphoric triamide and dimethyl sulfoxide, halogen solvents such as methylene chloride, chloroform, dichloroethane, trichloroethane and trichloroethylene and freon solvents. Of these, water is the most desirable from the standpoints of economic factors, convenience of handling and chemical stability. These solvents can also be used in mixtures of two or more.

The basic and acidic solutions that are used in this invention may also contain components other than the basic or acidic substances and the solvents.

In this invention, after the molded product has been subjected to treatment with bases or acids, the basic or acidic substance can be removed by washing.

Various inorganic and organic solvents can be used as washing solvents. For example, they can include water, various alcohols such as methanol, ethanol, propanol, 2-propanol, butanol, ethylene glycol, diethylene glycol, triethylene glycol, tetraethylene glycol, polyethylene glycol and glycerol, various aromatic hydrocarbons such as benzene, toluene and xylene, various aliphatic hydrocarbons such as hexane, heptane, octane, decane, petroleum ether, kerosene, ligroin and paraffin, various ketones such as acetone, methyl ethyl ketone and methyl isobutyl ketone, various esters such as ethyl acetate, butyl acetate, methyl benzoate and dioctyl phthalate, various ethers such as diethyl ether, tetrahydrofuran, dioxane, ethylene glycol dialkyl ether, diethylene glycol dialkyl ether, triethylene glycol dialkyl ether, tetraethylene glycol dialkyl ether and polyethylene glycol dialkyl ether, various nonprotonic polar solvents such as dimethylformamide, dimethylacetamide, N-methyl-2-pyrrolidone, dimethylimidazolidinone, hexamethyl phosphoric triamide and dimethyl sulfoxide, halogen solvents such as methylene chloride, chloroform, dichloroethane, trichloroethane and trichloroethylene and freon solvents.

Mixtures of two or more of these solvents can be used as the washing solvent. The washing solvent may contain components other than the solvents, for example, inorganic salts, surfactants and detergents.

The entire molded product may be subjected to said modification treatment or it may be performed on only a portion of the molded product, for example, the surface. When only the surface is subjected to modification treatment, the aqueous wetting property of the surface can be improved without making great changes in the physical properties of the molded product as a whole.

The tensile modulus of elasticity of the polymers of this invention should be less than 800 kPa. Their oxygen permeability should be an oxygen permeability coefficient greater than $60 \times 10^{-11}$ $(cm^2/sec)$ $mLO_2/(mL \cdot hPa)$.

The polymers of this invention are particularly suited for ophthalmic lenses such as contact lenses, intraocular lenses and artificial corneas.

EXAMPLES

We shall now describe this invention in specific terms by means of examples. However, this invention is not limited by them.

Determination Methods

The various determinations in these examples were performed by the methods described below.
(1) Oxygen Permeability Coefficient The oxygen permeability coefficient of a sample in the shape of a contact lens in water at 35° C. was determined using a Seikaken-shiki film oxygen permeability meter manufactured by SEIKI KOGYO Co., Ltd.
(2) Tensile Modulus of Elasticity A sample (array-type with a width in the vicinity of the center of on the order of 5 mm and a length on the order of 14 mm) cut from a contact lens shape using a stipulated punch mold was used, and determinations were made using a Model RTM-100 TENSILON manufactured by TOYOBALDWIN Co., Ltd. The drawing rate was set to 100 mm/min and the distance between grips was set to 5 mm.

Example 1

48.75 parts by weight of SiMAA, 16.25 parts by weight of TRIS, 35 parts by weight of DMAA, 1 part by weight of triethylene glycol dimethacrylate and 10 parts by weight of diethylene glycol dimethyl ether as the solvent were mixed homogeneously and 0.2 part by weight 2-hydroxy-2-methylpropiophenone (brand name, Darocure 1173; manufactured by CIBA Specialty Chemicals Inc.), after which this monomer mixture was deaerated in an argon atmosphere.

It was then poured into a plastic mold in a glove box with a nitrogen atmosphere and the mold was sealed. It was polymerized by irradiation (intensity of irradiation: 1 $mW/cm^2$, 30 minutes) using an insect attraction lamp. Following that, it was immersed together with the molds in diethylene glycol dimethyl ether, being immersed at 40° C. for 30 minutes and then at 60° C. for 60 minutes, after which it was released from the mold and a plastic molded product in the shape of a contact lens was obtained.

Following that, the diethylene glycol dimethyl ether was replaced with isopropyl alcohol and extraction of the remaining monomer was performed for 16 hours at 60° C. Following that, the plastic molded product was washed two times with isopropyl alcohol, after which it was first immersed in isopropyl alcohol/purified water=50/50 (parts by weight) for 30 minutes and was next immersed in isopropyl alcohol/purified water=25/75 (parts by weight) for 30 minutes. It was then allowed to stand immersed in purified water for 16 hours, with the isopropyl alcohol being completely removed from the plastic molded product.

The aforementioned plastic molded product was immersed for 8 hours at 40° C. in a 5 wt % aqueous solution (pH 2.6) of polyacrylic acid (average molecular weight: 150,000). Following that, said plastic molded product was thoroughly washed with purified water, after which it was immersed in boric acid buffer solution (pH 7.1 to 7.3) in a vial, and the vial was hermetically sealed. Said vial was introduced into an autoclave and was subjected to boiling treatment for 30 minutes at 120° C. It was then allowed to cool, after which the plastic molded product was removed from the vial and was immersed in boric acid buffer solution (pH 7.1 to 7.3). The oxygen permeability coefficient of this plastic molded product was $63 \times 10^{-11}$ $(cm^2/sec)$ $mLO_2/(mL \cdot hPa)$ and its modulus of elasticity was 662 kPa. The molded product that was obtained was transparent and was not turbid.

Examples 2 to 6

Plastic molded products in the shape of a contact lens were obtained by the same method as in Example 1 except that the mixture ratios of SiMAA, TRIS and DMAA were varied as shown in the table below. The plastic molded products that were obtained were all transparent and were not turbid. Their oxygen permeability coefficients [$\times 10^{-11}$ $(cm^2/sec)$ $mLO_2/(mL \cdot hPa)$] and their tensile moduli of elasticity [kPa] are shown in Table 1 below. All of the molded products had high oxygen permeability and low moduli of elasticity.

Comparative Example 1

A plastic molded product in the shape of a contact lens was obtained by the same method as in Example 1 except that TRIS was not added and that 65 parts by weight of SiMAA and 35 parts by weight of DMAA were used. The oxygen permeability coefficient [$\times 10^{-11}$ $(cm^2/sec)$ $mLO_2/(mL \cdot hPa)$] and the tensile modulus of elasticity [kPa] of the molded product that was obtained are shown in Table 1 below.

Comparative Example 2

A plastic molded product in the shape of a contact lens was obtained by the same method as in Example 1 except that SiMAA was not added and that 65 parts by weight of TRIS and 35 parts by weight of DMAA were used. The oxygen permeability coefficient [$\times 10^{-11}$ ($cm^2$/sec) $mLO_2$/(mL·hPa)] and the tensile modulus of elasticity [kPa] of the molded product that was obtained are shown in Table 1 below.

TABLE 1

|  | Content (parts by weight) | | | Oxygen permeability | Tensile modulus of elasticity |
| --- | --- | --- | --- | --- | --- |
|  | SiMAA | TRIS | DMAA | coeff. × $10^{-11}$ | (kPa) |
| Example 1 | 48.75 | 16.25 | 35 | 63 | 662 |
| Example 2 | 43.33 | 21.67 | 35 | 65 | 717 |
| Example 3 | 32.5 | 32.5 | 35 | 71 | 765 |
| Example 4 | 21.67 | 43.33 | 35 | 74 | 696 |
| Example 5 | 31.5 | 31.5 | 37 | 68 | 517 |
| Example 6 | 21 | 42 | 37 | 71 | 610 |
| Comp. Ex. 1 | 65 | 0 | 35 | 56 | 558 |
| Comp. Ex. 2 | 0 | 65 | 35 | 86 | 878 |

Industrial Applicability

By means of this invention, polymers of high oxygen permeability and a low modulus of elasticity are provided.

By using the polymers of this invention, ophthalmic lenses such as contact lenses, intraocular lenses and artificial corneas of high oxygen permeability and a low modulus of elasticity are provided.

What is claimed is:

1. Polymers characterized in that they are obtained by copolymerizing 5 to 90 parts by weight of siloxyanyl monomer (SiMAA) represented by the formula below, 5 to 90 parts by weight of 3-tris (trimethylsiloxy)silyl propyl methacrylate (TRIS), 5 to 70 parts by weight of N,N-dimethyl acrylamide (DMAA) and 0.1 to 3 parts by weight of monomer having two or more copolymerizable carbon-carbon unsaturated bonds in 1 molecule (provided that the total quantity of SiMAA, TRIS and DMAA is 100 parts by weight and that the total quantity of SiMAA and TRIS 30 to 95 parts by weight) and comprise a tensile modulus of elasticity is less than about 800 kPa.

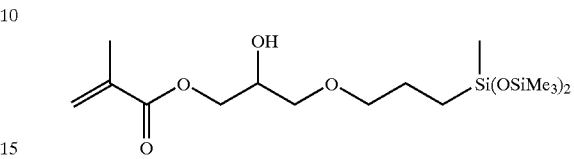

2. Polymers as set forth in claim 1 in which 5 to 50 parts by weight of SiMAA, 5 to 59 parts by weight of TRIS, 36 to 50 parts by weight of DMAA and 0,.1 to 3 parts by weight of monomer having two or more copolymerizable carbon-carbon unsaturated bonds in 1 molecule are copolymerized (provided that the total quantity of SiMAA, TRIS and DMAA is 100parts by weight and that the total quantity of SiMAA and TRIS is 50 to 64 parts by weight).

3. Ophthalmic lenses in which the polymers set forth in claim 1 are used.

4. Ophthalmic lenses as set forth in claim 3 in which the ophthalmic lenses are contact lenses.

5. Ophthalmic lenses as set forth in claim 3 that are subjected to surface modification by treatment with bases or treatment with acids.

* * * * *